(12) United States Patent
Ashe

(10) Patent No.: US 6,856,823 B2
(45) Date of Patent: Feb. 15, 2005

(54) SPIRAL MAGNETIC TRANSMITTER FOR POSITION MEASUREMENT SYSTEM

(75) Inventor: Westley Ashe, Milton, VT (US)

(73) Assignee: Ascension Technology Corporation (*) Notice: Subject to any disclaimer, the term of this patent is extended or adjusted under 35 U.S.C. 154(b) by 274 days.

(21) Appl. No.: 10/173,428

(22) Filed: Jun. 18, 2002

(65) Prior Publication Data

US 2003/0233042 A1 Dec. 18, 2003

(51) Int. Cl.[7] ................................................. A61B 5/05
(52) U.S. Cl. ........................................ 600/409; 600/407
(58) Field of Search ................................. 600/409, 410, 600/411, 424, 425, 407, 2, 20, 27, 32; 324/307, 308, 309

(56) References Cited

U.S. PATENT DOCUMENTS

| | | | | |
|---|---|---|---|---|
| 3,735,247 A | * | 5/1973 | Harker | 324/226 |
| 4,114,606 A | * | 9/1978 | Seylar | 600/409 |
| 5,158,932 A | * | 10/1992 | Hinshaw et al. | 505/162 |
| 5,198,768 A | | 3/1993 | Keren | |
| 5,323,777 A | * | 6/1994 | Ahonen et al. | 600/409 |
| 5,600,330 A | | 2/1997 | Blood | |
| 5,640,170 A | | 6/1997 | Anderson | |
| 5,669,383 A | * | 9/1997 | Johnson | 600/434 |
| 5,752,513 A | | 5/1998 | Acker et al. | |
| 6,208,884 B1 | * | 3/2001 | Kumar et al. | 600/409 |
| 6,496,713 B2 | * | 12/2002 | Avrin et al. | 600/409 |
| 6,690,963 B2 | * | 2/2004 | Ben-Haim et al. | 600/424 |

* cited by examiner

Primary Examiner—Daniel Robinson
(74) Attorney, Agent, or Firm—H. Jay Spiegel

(57) ABSTRACT

A transmitter consists of a plurality of magnetic transmitters, each of which is substantially planar and made of a spiral shaped conductor. The result is a transmitter having a substantially uniform cross-sectional current density along the radial direction of the spiral from the center to the periphery. Near the plane of a given spiral, magnetic vectors produced by such a conductor arrangement have improved angular characteristics as compared to prior art systems. This results in a larger region with useful vector crossing angles and operation of the system is enhanced as compared to prior art techniques. The transmitters produce magnetic fields which have a monotonically increasing intensity as one approaches the center of the transmitter spiral from any given direction. This feature simplifies and increases the accuracy of sensor position determination. If desired, the turns of the spiral transmitter may become closer together as one goes from the periphery to the center thereof to thereby concentrate the magnetic field more centrally of the transmitter. Transmitters having one or two spiral coils are also contemplated.

19 Claims, 4 Drawing Sheets

SPIRAL MAGNETIC TRANSMITTER FOR POSITION MEASUREMENT SYSTEM

BACKGROUND OF THE INVENTION

The present invention relates to a spiral magnetic transmitter for position measurement system. The present invention is generally in the field relating to devices for measuring the position of receiving antennas with respect to transmitting antennas using magnetic fields. Some such systems are able to measure position and orientation in six degrees of freedom, including translative motion in the three coordinate directions x, y and z, and orientation in the three orientation coordinates pitch, roll and azimuth. The present invention is equally applicable to systems designed to measure in fewer or greater than six degrees of freedom.

In the prior art, it is known to use magnetically based position and orientation measuring systems in the fields of biomechanics and medical diagnostics. In those fields, a sensor assembly is mounted on a point of interest and the position of that point is determined relative to a fixed transmitter to precisely show the relative motions of the point in question. In the medical environment, such systems are used to precisely locate an instrument or other object within the human body, thereby permitting complex methods of surgery and diagnostics to be carried out where accuracy in location is essential. In such applications, it is advantageous to provide a transmitting means that is relatively small and does not interfere with the therapeutic procedure that is taking place.

It is also known to make magnetic transmitters that are flat. In the prior art, a plurality of dipole or non-dipole transmitters are arranged conveniently to produce a field pattern that is useful in determining object position. However, when the sensor approaches the plane of the transmitter loops, position and orientation measurement become difficult as the vectors from the transmitter loops become highly parallel.

Dipole systems also suffer from the phenomenon of magnetic cross-coupling, as the magnetic field from one dipole element induces current in another adjacent element which induced current is then re-radiated by that element, thereby producing undesirable field distortions. Methods of preventing or eliminating such re-radiations are known in the art but require increased complexity in transmitter driver circuitry. Prior art non-dipole systems also suffer from this re-radiation effect. Additionally, in the case of the prior art non-dipole systems, the shape of the equi-potential surface of the vector magnitude also changes from spherical to toric as distance from the transmitter loops decreases. This phenomenon causes numerous difficulties when attempting to determine position and/or orientation of an object within a prescribed space.

The following prior art is known to Applicant:

U.S. Pat. No. 5,600,330 to Blood discloses a non-dipole loop transmitter based magnetic tracking system which utilizes formed elongate conductor patterns which describe a loop. In the Blood system, when the sensor approaches the plane of the transmitter loops, position determination becomes difficult and unstable as the vectors from the transmitter loops become parallel. The shape of the equi-potential surface of the vector magnitude also changes from spherical to toric as distance from the transmitter loops decreases. This causes numerous difficulties in finding a position and/or orientation solution. Blood fails to teach or suggest a method of finding position and orientation using a planar spiral antenna and such an antenna is nowhere disclosed by Blood.

U.S. Pat. No. 5,752,513 to Acker et al. discloses a method and apparatus for determining position of an object. Acker et al. disclose use of an elongated thin conductor as the transmitting element and various antenna configurations. All of those configurations are effectively formed from the equivalent of elongate loop conductors with the current carrying components of the transmitter means residing substantially along the outer boundary of the transmitter means. Acker et al. disclose overlapping adjacent transmitter loops but the methods disclosed by Acker et al. inherently result in significant cross-coupling of the coil axes. Acker et al. fail to teach or suggest any method of reducing the undesirable cross-coupling that occurs.

U.S. Pat. No. 5,198,768 to Keren discloses a surface coil array for use in nuclear magnetic resonance applications. Keren fails to determine position nor does Keren describe methods of reducing cross-coupling between adjacent coils.

U.S. Pat. No. 5,640,170 to Anderson discloses a transmitter configuration employing a spiral conductor pattern over a conductive ground plane in order to produce a low distortion dipole field over the configuration. The Anderson device cannot be used in a planar configuration as it requires that a conventional two axis dipole be located above the spiral or that multiple spirals intersect at right angles. Either one of these options results in an increased transmitter profile. Anderson discloses that operation of the Anderson system results from a new previously undiscovered principle of boundary condition behavior but fails to disclose methods to minimize cross-coupling effects from additional axes which may be employed by the system.

Additionally, the present invention represents a distinct departure from the prior art known to Applicant relating to transmitting and receiving position and orientation devices since the present invention is capable of satisfying the requirement of operation near the plane of the transmitter and operates using conventional boundary condition physics while not requiring special current densities or conductive planes. The present invention operates with either dipole or non-dipole transmitted fields. Additionally, a method of construction is disclosed which results in the ability to arrange up to three transmitter coils which overlap but are free from undesirable cross-coupling.

SUMMARY OF THE INVENTION

The present invention relates to a spiral magnetic transmitter for position measurement system. In the present invention, the disclosed transmitters have enhanced operation when the sensor approaches the transmitter plane. The transmitters disclosed may measure position and orientation in up to six degrees of freedom including the x, y and z position coordinates as well as the orientation coordinates azimuth, elevation and roll.

In one embodiment of the present invention, the transmitter means consists of a plurality of magnetic transmitters, each of which is substantially planar and made of a spiral shaped conductor. The result is a transmitter having a substantially uniform cross-sectional current density along the radial direction of the spiral from the center to the periphery. Near the plane of a given spiral, magnetic vectors produced by such a conductor arrangement have improved angular characteristics as compared to prior art systems. This results in a larger region with useful vector crossing angles and operation of the system is enhanced as compared to prior art techniques.

The transmitters disclosed herein produce magnetic fields which have a monotonically increasing intensity as one approaches the center of the transmitter spiral from any given direction. This feature simplifies position and orientation calculations and increases the accuracy of sensor position and orientation determination. For a given magnetic field level and a given point relative to the transmitter, the current density in a spiral coil will be lower than for a conventional coil as the spiral transmits magnetic field over a greater area. This decreased current density is advantageous when the transmitter is operated over a permeable barrier since the barrier can be made thinner for a given flux density level, thereby decreasing weight and cost.

As the angles between magnetic field vectors from respective transmit axes become more parallel, the position solution becomes more sensitive to error sources such as noise or field distortion. When using a loop shaped antenna, regions near the plane of the loop have their magnetic vectors nearly perpendicular to the loop plane. When such loops are arranged to form a multiple axis planar transmitter, the solution for position inside of about 0.25 loop radii becomes increasingly sensitive as a result of increasingly parallel vectors. In the spiral antennas used in accordance with the teachings of the present invention, the vectors are parallel to the spiral plane when very close to the antenna, and point radially away from the center. This results in a much more favorable included angle, and allows position to be reliably determined essentially all the way to the antenna plane.

If desired, the turns of the spiral transmitter may become closer together as one goes from the periphery to the center thereof to thereby concentrate the magnetic field more centrally of the transmitter.

As such, it is a first object of the present invention to provide a spiral magnetic transmitter for position measurement system.

It is a further object of the present invention to provide such a transmitter which quantitatively measures the position of receiving antennas relative to transmitting antennas without the disadvantages of non-spiral transmitters.

It is a still further object of the present invention to provide such a transmitter system in which the intensity of the magnetic field vectors changes monotonically with respect to the distance from the center of a given transmitting element.

It is a still further object of the present invention to provide such a transmitter which avoids the issue of unfavorable crossing angles of magnetic vectors adjacent the transmitter plane as is the case in prior art transmitters.

It is a still further object of the present invention to provide such a transmitter which facilitates operation without the requirement of conductive ground planes in close proximity to the transmitter.

It is a still further object of the present invention to provide such a system which can utilize either dipole or non-dipole transmitted magnetic fields.

It is a still further object of the present invention to provide such a system which facilitates more efficient use of a permeable barrier material so that a permeable barrier material, if used, can be thinner than is the case in the prior art systems.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

Figure 1:
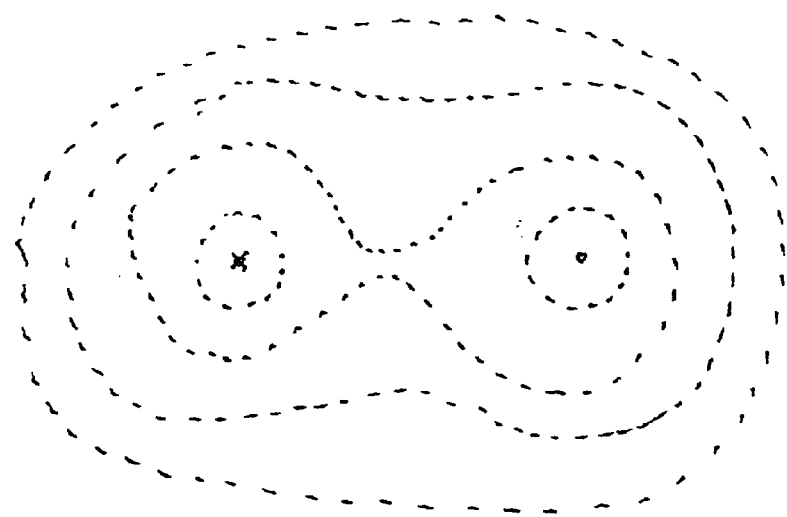
FIG. 1 shows a simulation result showing equi-potential surface shapes for a prior art non-dipole loop system.

Reference is first made to FIG. 1 which shows various equi-potential surface shapes as for a prior art non-dipole system consisting of a single loop antenna. As is clear from FIG. 1, the field equi-potential contours change from substantially spherical to substantially toric in shape as the loop wires are approached. A highly desirable method of determining position is to determine the vector magnitude from each transmitter element, which determines a surface representing the possible locations of the sensor relative to that element. If the surface is a spheroid, the surfaces from 3 transmit antennas will intersect at only 2 points, one above and one below the plane of the transmitter. Provided that there is a method to determine which of the 2 points the sensor is located at, the actual position is then determined. Those skilled in the art are familiar with this property known as hemispheric ambiguity, and methods of determining which of the 2 possible points is the actual position is well described in the art. When the field equi-potential contours become toric, the surfaces no longer intersect at only 2 points, and reliable position solutions require additional redundant information, such as additional transmitters or information regarding the last known sensor position which can seed a convergence algorithm. These additional items complicate the system and generally decrease its reliability.

Figure 2:
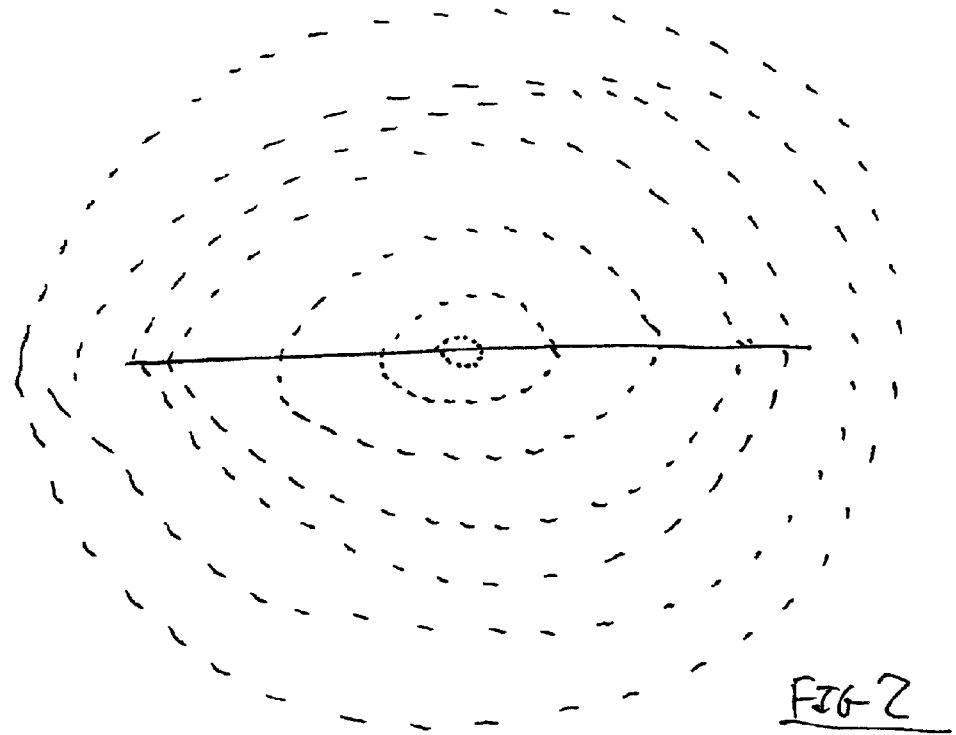
FIG. 2 shows a simulation result showing equi-potential surface shape for a transmitter spiral in accordance with the teachings of the present invention.

By contrast, FIG. 2 shows the equi-potential surface shape for a spiral transmitter in accordance with the teachings of the present invention. The equi-potential surface shape is regular and predictable and consistent from the center thereof to the periphery. Where three spiral transmitters are provided and their configuration is such that they overlap and intersect, there is one intersecting point in each hemisphere for all three transmitters. By contrast, in the prior art single loop antenna corresponding to the equi-potential surface shape of FIG. 1, there are multiple intersecting points in each hemisphere and therefore multiple solutions, thereby introducing inaccuracies into position and orientation calculations.

Figure 3:
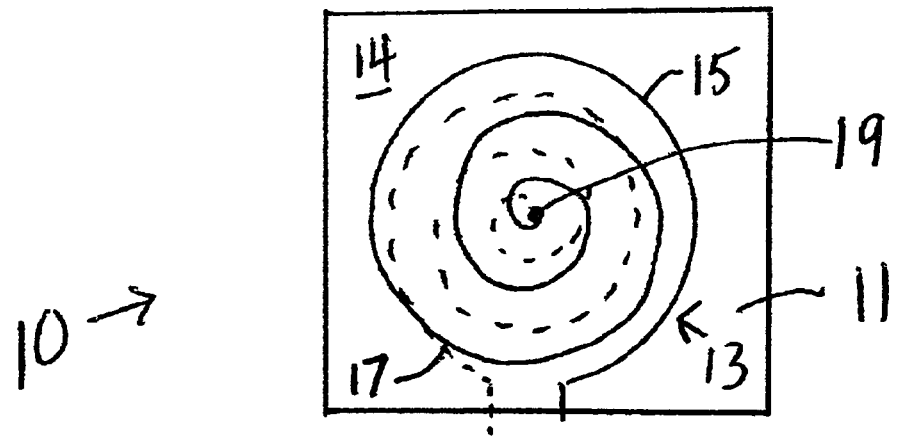
FIG. 3 shows a top view of a first embodiment of transmitter in accordance with the teachings of the present invention.

With reference now to FIG. 3, a first embodiment of antenna in accordance with the teachings of the present invention is generally designated by the reference numeral 10 and is seen to include a substrate 11 that may comprise a PC board, and a transmitter generally designated by the reference numeral 13 including a spiral shape 15 mounted on the top surface 14 of the PC board, and a corresponding spiral shape 17 shown in phantom mounted on the bottom surface of the PC board. The shapes 15 and 17 are connected by a feed through 19 at the center thereof.

Figure 4:
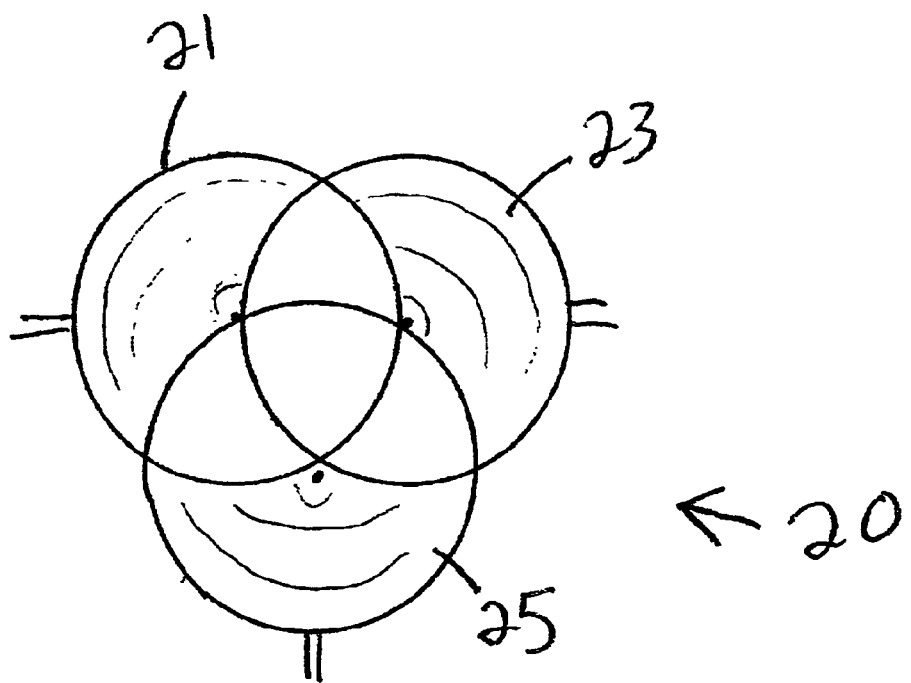
FIG. 4 shows a top view of a second embodiment of transmitter.
Figure 5:
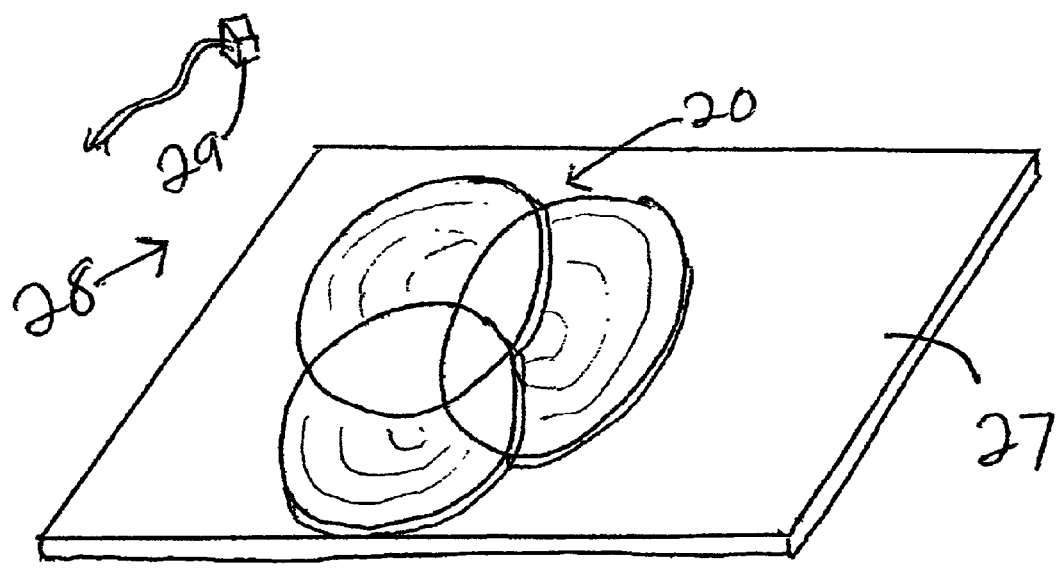
FIG. 5 shows a perspective view of the transmitter of FIG. 4 as mounted on a substrate.
Figure 6:
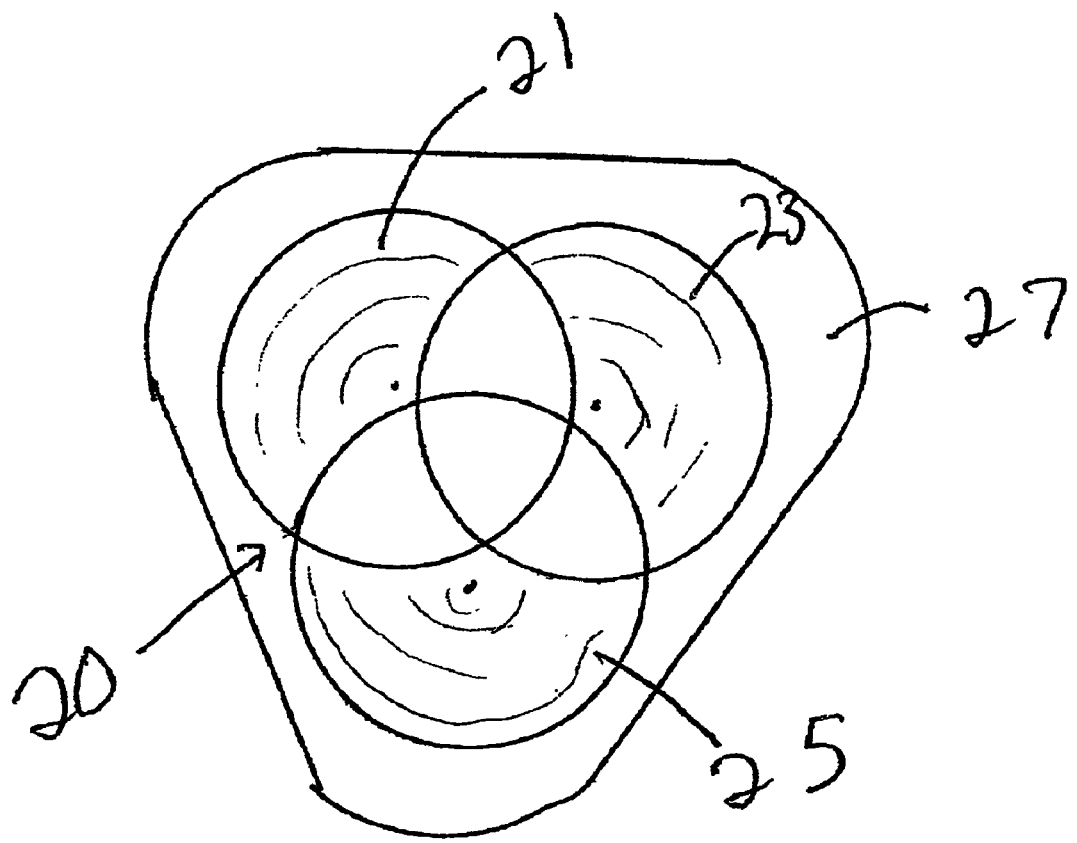
FIG. 6 shows a top view of the transmitter of FIGS. 4 and 5 as mounted on a substrate.

With reference to FIGS. 4–6, a second embodiment of transmitter is generally designated by the reference numeral 20 and is seen to include three spiral transmitter coils 21, 23 and 25 associated with one another in overlapping configuration as shown in FIG. 4.

As seen in FIG. 5, the transmitter 20 may be mounted on a substrate 27 such as, for example, a PC board. If desired, in keeping with the teachings of FIG. 3, each of the spiral coils 21, 23 and 25 may also be coupled to an additional coil mounted beneath the substrate 27 and electrically connected to each respective one of the coils 21, 23 or 25 by respective feed throughs (not shown).

FIG. 6 shows a top view of the configuration shown in FIG. 5.

In one preferred configuration, the transmitters 10, 21, 23 and 25 may be constructed of a radius of 5 inches each consisting of two layers of conductor with 67 turns per layer and a pitch of 0.075 inches. Such a transmitter has an inductive of about 1.53 mH and a DC resistance of approximately 5.2 Ohms.

FIGS. 4–6 show overlapping transmitters. The degree of overlap may be adjusted such that the coupling coefficient between each of the three spiral transmitters is essentially zero. This ensures that when a given spiral transmitter is energized, parasitic currents do not flow in the remaining spiral transmitters. Such parasitic currents would otherwise be re-radiated by the other two transmitters, thereby causing undesirable distortions in the magnetic field emitted by the magnetic transmitter that is energized.

Under certain circumstances, the benefits of arranging multiple spiral transmitters in a different manner may outweigh the advantages of arranging them to create a zero cross-coupling arrangement. For example, arrangements requiring four or more transmitters comprising a magnetic transmitter may be utilized if a larger operating volume is required or if redundant information in the calculated solution is needed to reduce errors due to metallic objects (not shown) located adjacent the measuring space. Additionally, spiral transmitters may be made relatively large with other non-dipole or dipole transmitters being conveniently arranged within the boundaries of the spiral transmitter. In this case, the spiral transmitter can provide favorable vector crossing angles near the plane of the magnetic spiral transmitter which improve the solution characteristics over those that are obtained using loop-type transmitters.

If desired, it may also be advantageous to locate the spiral transmitters 21, 23 and 25 in something other than a co-planar configuration, if this proves convenient and improves the characteristics for a given application. Examples of alternative configurations can include locating the transmitters in spaced parallel planes, different planes that are not parallel, or in planes angled with respect to one another.

It is also possible within the purview of the present invention to construct each transmitter with a non-uniform pitch from the center to the periphery. For example, the number of turns per radial inch can be increased as one goes from the periphery to the center of the transmitter. Such a construction detail is employed to tailor the magnetic field characteristics to better fit a particularly chosen mathematical model.

In conducting position and orientation measurements using transmitters in accordance with the teachings of the present invention, each spiral transmitter is energized in a manner which allows its field to be distinguishable from the magnetic fields emitted by the other spiral transmitters. Such methods of orthogonal energization are well known to those skilled in the art.

FIG. 5 shows a sensor 29 designed to sense magnetic fields emanating from the transmitters 21, 23 and 25. The sensor 29 detects the value of the magnetic field vector produced by one of the spiral transmitters at a point of interest in the measurement space 28 (FIG. 5). Numerous methods familiar to those skilled in the art exist which permit sensed magnetic fields to be converted to sensor position and orientation. The only requirement is that the number of transmitter axes times the number of sensor axes be at least equal to the desired number of degrees of freedom to be measured. Traditionally, the six degrees of freedom consist of the x, y and z axes as well as the orientation coordinates azimuth, elevation and roll.

An important aspect of the present invention is that immediately above a spiral transmitter, the magnetic field vector directions become more parallel to the spiral transmitter than is the case when compared to a conventional loop transmitter. The nature of the spiral transmitter is that of a planar distributed source which is fundamentally different from prior art systems which concentrate their field generating elements in a small area. One advantage of the present invention is that adjacent to and immediately above the plane of a spiral transmitter, the magnetic field values are parallel to the spiral transmitter. As a result, favorable vector crossing angles exist when operating over at least one of the spiral transmitter coils of the transmitter. As a result, the position solution may be obtained with significantly less mathematical sensitivity than is obtained with prior art loop-type transmitters, either dipole or non-dipole.

Table 1 shows the included angle of the magnetic vector as a function of radius for a 100 mm radius spiral and for a loop transmitter coil. In the Table, the periphery of each antenna is defined as 100 mm from the center thereof. The figures in the Table above 100 mm consist of figures within the measuring space beyond the periphery of the antenna, in each case.

TABLE 1

| Radius, mm | Spiral | Loop |
|---|---|---|
| 0 | 90 | 90 |
| 10 | 76 | 89 |
| 20 | 68 | 88 |
| 30 | 59 | 87 |
| 40 | 52 | 86 |
| 50 | 45 | 84 |
| 60 | 35 | 82 |
| 70 | 22 | 78 |
| 80 | 9 | 75 |
| 90 | −11 | 51 |
| 100 | −41 | 6.2 |
| 110 | −59 | −36 |
| 120 | −64 | −56 |
| 130 | −70 | −78 |
| 200 | −85 | −83 |

As should be clear from Table 1, the crossing angles of the magnetic field are much more distinct in the case of the spiral antenna than is the case with the loop antenna, thereby rendering position and orientation measurements much more accurate and unambiguous.

As such, an invention has been disclosed in terms of preferred embodiments thereof which fulfill each and every one of the objects of the invention as set forth hereinabove, and provide a new and useful spiral antenna system for position measurement of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

What is claimed is:

1. In a position measurement system, the improvement comprising a transmitter including a first conductor arranged in a first planar spiral having a plurality of turns, a second conductor arranged in a second planar spiral having a plurality of turns, and sensing means attached to an object for sensing magnetic fields emanating from said spirals and therefrom calculating position of said object in a space, said first and second spirals being mounted on respective opposed parallel faces of a substrate, one spiral directly overlying another spiral, said system measuring position in a number of degrees of freedom at most equal to a number of transmitter axes times a number of sensor means axes.

2. The system of claim 1, wherein each spiral has adjacent conductor rings that are substantially concentric.

3. The system of claim 1, wherein each spiral has adjacent conductor rings, spacing between adjacent conductor rings becoming smaller toward a center of each spiral.

4. The system of claim 1, wherein said spirals are electically connected through said substrate.

5. The system of claim 1, wherein each of said first and second spirals consists of a first spiral half located on one face of said substrate and a second spiral half located on another face of said substrate aligned with said first spiral half.

6. The system of claim 1, further including a third planar spiral, said spirals overlapping one another.

7. The system of claim 6, wherein each of said spirals consists of a first spiral half located on one face of a substrate and a second spiral half located on another face of said substrate aligned with said first spiral half.

8. The system of claim 7, wherein spiral halves on each face of said substrate are co-planar.

9. The system of claim 6, wherein each spiral has adjacent conductor rings that are substantially concentric.

10. The system of claim 6, wherein each spiral has adjacent conductor rings, spacing between adjacent conductor rings becoming smaller toward a center of each spiral.

11. In a position measurement system, the improvement comprising a transmitter including a first conductor arranged in a first planar spiral having a plurality of turns, a second conductor arranged in a second planar spiral having a plurality of turns, and a third conductor arranged in a third planar spiral having a plurality of turns, said spirals being mounted on a substrate having opposed parallel faces, and sensing means attached to an object for sensing magnetic fields emanating from said spirals and therefrom calculating position of said object in a space, said system measuring position in a number of degrees of freedom at most equal to a number of transmitter axes times a number of sensor means axes, said spirals overlapping one another and lying in a common plane.

12. The system of claim 11, wherein each spiral has adjacent conductor rings that are substantially concentric.

13. The system of claim 11, wherein each spiral has adjacent conductor rings, spacing between adjacent conductor rings becoming smaller toward a center of each spiral.

14. The system of claim 11, wherein each of said spirals consists of a first spiral half located on one face of said substrate and a second spiral half located on another face of said substrate aligned with said first spiral half, said spiral halves being electrically connected through said substrate.

15. In a position measurement system, the improvement comprising a transmitter including a first conductor arranged in a first planar spiral having a plurality of turns, a second conductor arranged in a second planar spiral having a plurality of turns, said first and second spirals being mounted on respective opposed parallel faces of a substrate, one spiral directly overlying another spiral, and sensing means attached to an object for sensing magnetic fields emanating from said spirals and therefrom calculating position of said object in a space, and a third planar spiral, said spirals overlapping one another, said system measuring position in a number of degrees of freedom at most equal to a number of transmitter axes times a number of sensor means axes.

16. The system of claim 15, wherein each of said spirals consists of a first spiral half located on one face of a substrate and a second spiral half located on another face of said substrate aligned with said first spiral half.

17. The system of claim 16, wherein spiral halves on each face of said substrate are co-planar.

18. The system of claim 15, wherein each spiral has adjacent conductor rings that are substantially concentric.

19. The system of claim 15, wherein each spiral has adjacent conductor rings, spacing between adjacent conductor rings becoming smaller toward a center of each spiral.

* * * * *